US008569037B2

(12) United States Patent
Tateishi et al.

(10) Patent No.: US 8,569,037 B2
(45) Date of Patent: Oct. 29, 2013

(54) FUNGUS HAVING ACTIVITY OF CONTROLLING DISEASE OF GRAMINEOUS PLANT, CONTROLLING AGENT USING THE SAME, METHOD OF CONTROLLING AND BIOLOGICAL MATERIAL

(75) Inventors: Hideaki Tateishi, Fukushima (JP); Yoneko Sakuma, Fukushima (JP)

(73) Assignee: Kureha Corporation, Tokyo (JP)

( * ) Notice: Subject to any disclaimer, the term of this patent is extended or adjusted under 35 U.S.C. 154(b) by 941 days.

(21) Appl. No.: 10/577,375

(22) PCT Filed: Oct. 29, 2004

(86) PCT No.: PCT/JP2004/016088
§ 371 (c)(1),
(2), (4) Date: Feb. 12, 2007

(87) PCT Pub. No.: WO2005/040358
PCT Pub. Date: May 6, 2005

(65) Prior Publication Data
US 2007/0259783 A1 Nov. 8, 2007

(30) Foreign Application Priority Data
Oct. 29, 2003 (JP) ................................ 2003-369280

(51) Int. Cl.
*C12N 1/20* (2006.01)
*A01N 63/00* (2006.01)
(52) U.S. Cl.
USPC ........................ 435/254.1; 424/93.5; 504/117
(58) Field of Classification Search
None
See application file for complete search history.

(56) References Cited

U.S. PATENT DOCUMENTS 5,770,787 A    6/1998   Montague et al.

FOREIGN PATENT DOCUMENTS

| JP | 04-295407 | 3/1991 |
| JP | 06-087716 | 9/1992 |
| JP | 09-124427 | 10/1995 |
| JP | 11-225747 | 2/1998 |
| JP | 11-225745 | 11/1998 |
| JP | 11-253151 | 11/1998 |
| JP | 2000-290113 | 10/2000 |
| WO | WO 95/14784 | 10/1994 |

OTHER PUBLICATIONS

Kim et al., 1990. Glucose oxidase as the antifungal principle of talaron from Talaromyces flavus. Can. J. Microbiol. 36: 760-764.*
Marois et al., Plant Diseases. vol. 66 No. 12, pp. 1166-1168, 1982.*
International Search Report for PCT/JP2004/016088, dated Feb. 1, 2005.
International Preliminary Report on Patentability for PCT/JP2004/016088. Feb. 1, 2005.
Fujii, Yuzo et al., "Penicillium decumbens kara no Ine Imochibyokin Melamin Gosei Sogai Busshitsu", Oct. 12, 2001 Nendo Nogei Kagukukai Kansai Nishinihon, Chushikoku Shibu Godo Taikai Koen Yoshishu (2001), p. 8, with English translation.
Fujii, Yuzo et al., "Penicillium decumbens kara no Ine Imochibyokin Melamin Gosei Sogai Busshitsu,—second report", 2002 Nendo (Heisei 14 Nendo) Nogei Kagukukai Taikai Koen Yoshishu, Mar. 5, 2002, p. 78, 3-2Cp11, with English translation.
Okeke, Boniface et al. "Fungal metabolite extracts active against phytopathogens", Sci. Total Environ. vol. 155, No. 2, 1994, pp. 125-130.
Renwick, A., "Assessment of in vivo screening systems for potential biocontrol agents of *Gaeumannomyces graminis*", Plant Pathology vol. 40, No. 4, 1991, pp. 524-532.
Koch, E., "Evaluation of commercial products for microbial control of soil-borne plant diseases", Crop Protection vol. 18, No. 2, 1999, pp. 119-125.
Stosz, Sarah K. et al., "In Vitro Analysis of the Role of Glucose Oxidase from *Talaromyces flavus* in Biocontrol of the Plant Pathogen *Verticillium dahliae*", Appl. Environ. Microbiol. vol. 62, No. 9, 1996, pp. 3183-3186.
Madi, Lea et al., "Biological control of *Sclerotium rolfsii* and *Verticillium dahliae* by *Talaromyces flavus* is mediated by different mechanisms", Phytopathology, vol. 87, No. 10, 1997, pp. 1054-1060.
EPO Supplementary European Search Report for Application No. 047931697.9-1212/1679367 PCT/JP2004016088, dated Jul. 28, 2008.
Fujii, Yuzo et al., "Fungal melanin inhibitor and related compounds from *Penicillium decumbens*", Phytochemistry, vol. 60, 2002, pp. 703-708.
Dewan, M.M. et al., "Occurrence of species of *Aspergillus* and *Penicillium* in roots of wheat and ryegrass and their effect on root rot caused by *Gaeumannomyces graminis* var. *tritici*", Aust. J. Bot., vol. 36, 1988, pp. 701-710.
Okeke, Boniface et al., "Identification of mycotoxin-producing fungal strians: a step in the isolation of compounds active against rice fingal diseases", J. Agric. Food Chemj., vol. 41, 1993, XP-002488287, pp. 1731-1735.
Extended European Search Report dated Mar. 17, 2010 for European Patent Application 10000108 (corresponds to U.S. Appl. No. 10/577,375.

* cited by examiner

*Primary Examiner* — Irene Marx
(74) *Attorney, Agent, or Firm* — Greenblum & Bernstein, P.L.C.

(57) ABSTRACT

It is intended to establish a technology of controlling Gramineous plant seed-borne disease that avoids the danger of development of resistant pathogeus, being highly safe to environment and stable. There is provided a fungus having activity of controlling fungal disease and bacterial disease occurring during the raising of rice plant seedling, and are further provided, using the fungus as an active ingredient, a controlling agent, method of controlling and biological material.

4 Claims, No Drawings

FUNGUS HAVING ACTIVITY OF CONTROLLING DISEASE OF GRAMINEOUS PLANT, CONTROLLING AGENT USING THE SAME, METHOD OF CONTROLLING AND BIOLOGICAL MATERIAL

TECHNICAL FIELD

The present invention relates to a fungus having activity of controlling damages caused by an infectious disease in a Gramineous plant, and a controlling agent, a controlling method, and a biological material using the fungus as an active ingredient. In more detail, the present invention relates to a fungus having activity of controlling fungal disease and bacterial disease occurring at the raising of rice plant seedlings, and a controlling agent, a controlling method, and a biological material using the fungus as an active ingredient.

BACKGROUND ART

As the damages caused by diseases during the raising of Gramineous plant seedlings, diseases caused by fungi such as *Gibberella fujikuroi, Cochliobolus miyabeanus*, and *Pyricularia oryzae*; and bacterial diseases caused by bacteria such as *Burkholderia glumae, Burkholderia plantarii*, and *Acidodovorax avenae* can be given. To control those diseases, a seed disinfectant, a soil drenching agent, a soil treatment agent, and a foliage spraying agent after greening are considered as effective, and a chemical pesticide is used alone or chemical pesticides are used in combination. For the diseases caused by fungi, highly effective EBI fungicides are used. For the diseases caused by a bacterium, an oxolinic acid or a copper (II) hydroxide is used. However, there arise some cases where stable effects may not be expected because of the appearance of resistant bacteria each having reduced sensitivity against those fungicides. Moreover, waste water of chemical pesticides has to be processed after the use thereof, resulting in problems such as burden on workers and costs required therein.

From said viewpoint, studies on biocontrol utilizing microorganisms, which are assumed to exhibit lower environmental burden than a chemical pesticide, have been progressed in recent years, and parts of them have been put into practical use. For controlling the above-mentioned seed-borne diseases, Patent Document 1 discloses a non-pathogenic *Pseudomonas glumae*, which is effective for the disease caused by *Burkholderia glumae*, and Patent Document 2 discloses that *Erwinia carotovora* having lost its pathogenicity is effective for controlling the disease caused by *Burkholderia plantarii*. Meanwhile, Patent Document 3 describes *Pseudomonas* sp. which is effective for diseases caused by *Burkholderia glumae, Burkholderia plantarii*, and *Gibberella fujikuroi*, and Non-patent Document 1 describes *Pseudomonas aureofaciens* which is effective for diseases caused by *Burkholderia glumae* and *Burkholderia plantarii*.

Meanwhile, Patent Document 4 discloses a microorganism belonging to the genus *Trichoderma*, which is effective for fungal disease caused by *Gibberella fujikuroi, Pyricularia oryzae*, or the like, and Patent Document 5 discloses a microorganism belonging to the genus *Trichoderma*, which is effective for a bacterial disease caused by *Burkholderia plantarii*.

While biocontrol generally utilizing a microorganism has been realized, however, controlling agents which are effective with a low administration amount, and which exhibit less environmental burden have been desired. However, even for the biological pesticides utilizing those microorganisms, it was difficult to control the damages caused by diseases such as fungi disease and bacteria disease and attain stable effects comparable to chemical pesticides.

Patent Document 1: JP-A-04-295407
Patent Document 2: JP-A-06-087716
Patent Document 3: JP-A-09-124427
Patent Document 4: JP-A-11-225745
Patent Document 5: JP-A-11-253151
Non-patent Document 1: "Biological Pesticide Test Score in 1999" (Japan Plant Protection Association, January 2000)

DISCLOSURE OF THE INVENTION

Problem to be Solved by the Invention

In view of the above circumstances, the present inventors have made studies to establish a stable technology for controlling seed-borne diseases of Gramineous plants, which is less fear of bringing a resistant bacterium into appear, and is highly safe to environment. As a result, they have found out a specific fungus having activity of controlling fungal disease and bacterial disease occurring during the raising seedling of the Gramineous plants, and thus have completed the present invention.

Means for Solving the Problem

The present invention relates to a fungus which is effective for seed-borne diseases of Gramineous plants, has activity of controlling fungal and bacterial diseases occurring during the raising seedling of the Gramineous plants, and belongs to the genus *Penicillium* or the genus *Talaromyces* or *Eupenicillium* which is the teleomorph of the genus *Penicillium*.

(1) A fungus, which has activity of controlling an infectious disease of a Gramineous plant, and belongs to the genus *Penicillium* or the genus *Talaromyces* or *Eupenicillium* which is a teleomorph of the genus *Penicillium*.

(2) The fungus according to the above item (1), in which the fungus is *Penicillium verruculosum*.

(3) The fungus according to the above item (1), in which the fungus is *Penicillium aculeatum*.

(4) The fungus according to the above item (1), in which the fungus is *Eupenicillium reticulisporum*.

(5) A *Penicillium* sp. B-453 (FERM BP-08517).

(6) A *Talaromyces* sp. B-422 (FERM BP-08516).

(7) An *Eupenicillium reticulisporum* B-408 (FERM BP-08515).

(8) An agent for controlling a disease of a Gramineous plant containing as an active ingredient at least one strain of the fungus according to any one of the above items (1) to (7).

(9) The agent for controlling a disease of a Gramineous plant according to the above item (8), in which the agent has activity of controlling both a fungal disease and a bacterial disease occurring at raising of a rice seedling.

(10) A method of controlling a disease of a Gramineous plant comprising using the agent for controlling a disease of a Gramineous plant according to the above item (8) or (9).

(11) A biological material treated with the agent for controlling a disease of a Gramineous plant according to the above item (8) or (9).

(12) The biological material according to the above item (11), in which the biological material is a soil for raising a seedling of a Gramineous plant.

(13) A plant seed treated with the agent for controlling a disease of a Gramineous plant according to the above item (8) or (9).

Effects of the Invention

According to the present invention, there is provided a biological pesticide, which is safe for environment, human, and livestocks, and has high controlling effect, thereby being capable of contributing to organic cultivation using reduced amounts of chemical pesticides. A microbial pesticide utilizing an antagonistic fungus of the present invention reduces economic losses of the farmers suffered from the occurrence of diseases in rice. The controlling effect equivalent to that obtained by a chemical pesticide can be obtained, while effectiveness against a resistant bacterium by which particular pesticides have lost their effects can be expected. In addition, the employment of the biological pesticide as an alternative for a chemical pesticide enables to reduce the release of chemical substances to environment.

BEST MODE FOR CARRYING OUT THE INVENTION

The fungus, which has activity of controlling a fungal or bacterial disease occurring at the raising seedlings of a Gramineous plant, used in the present invention includes funguses belonging to the genus *Penicillium*, and microorganisms belonging to the genera *Talaromyces* and *Eupenicillium* which is the teleomorph of the genus *Penicillium*.

Examples of the microorganism belonging to the genus *Penicillium* preferably include *Penicillium verruculosum* and *Penicillium aculeatum*, and more preferably *Penicillium* sp. B-453. Note that, the present strains were deposited in International Patent Organism Depositary, National Institute of Advanced Industrial Science and Technology, Tsukuba Central 6, 1-1-1 Higashi, Tsukuba, Ibaraki, Japan on Oct. 20, 2003 (FERM BP-08617).

Furthermore, an example of the microorganism belonging to the genus *Eupenicillium* preferably includes *Eupenicillium reticulisporum* B-408. Note that, the present strains were deposited in International Patent Organism Depositary of National Institute of Advanced Industrial Science and Technology, Tsukuba Central 6, 1-1-1 Higashi, Tsukuba, Ibaraki, Japan on Oct. 20, 2003 (FERM BP-08515).

In addition, an example of the microorganism belonging to the genus *Talaromyces* preferably includes *Talaromyces* sp. B-422. Note that, the present strains were deposited in International Patent Organism Depositary of National Institute of Advanced Industrial Science and Technology, Tsukuba Central 6, 1-1-1 Higashi, Tsukuba, Ibaraki, Japan on Oct. 20, 2003 (FERM BP-08516).

For instance, *Talaromyces* sp. B-422 is a microorganism which was isolated from a rice seedling. *Talaromyces* sp. B-422 grows well in a PDA medium, and forms conidia and gymnothecia like the genus *Penicillium*. The conidia grow to unicellular, short-elliptic forms, forming chains. Ascospores are elliptic and have rough to spinous surfaces.

*Eupenicillium reticulisporum* B-408 was also isolated from a rice seedling. *Eupenicillium reticulisporum* B-408 grows well in a PDA medium and forms conidia like the genus *Penicillium*. The conidia grow to unicellular, spherical and subspherical forms, forming chains.

*Penicillium* sp. B-453 was also isolated from a rice seedling. *Penicillium* sp. B-453 grows well in a PDA medium and forms conidia like the genus *Penicillium*. The conidia grow to unicellular, spherical and subspherical forms, forming chains.

Those microorganisms were identified as described above by virtue of the fact that the microorganisms exhibited the same properties on a medium, morphological properties, and physiological properties as those shown by the corresponding species of fungi, respectively. Those microorganisms have extremely excellent activity of controlling the fungal of bacterial disease occurring during the raising seedling of a Gramineous plant as described below.

In addition, those microorganisms proliferated by known means such as culture with a material such as bran, static culture in a solid medium, liquid culture may be used, and the microorganisms are not limited particularly by the kinds of medium, culture conditions, and the like.

In the present invention, the amount of the fungus to be used is appropriately selected depending on the form of formulation, the application method, the crop and location to which the fungus is applied, the kinds of disease to which the fungus is applied, or the like. However, the fungus is desirably used in the range of $1\times10^2$ to $1\times10^{11}$/ml of spore concentration, and preferably $1\times10^4$ to $1\times10^8$/ml.

The agent for controlling a disease of a Gramineous plant of the present invention contains as an active ingredient a culture solution or suspension of those microorganisms. The culture solution or suspension may be used without any modification. Alternatively, the microorganisms are mixed with, for example, a solid or liquid carrier and then a commonly-used additive or other aid is added thereto as required, to thereby prepare a formulation.

The controlling method utilizing the agent for controlling a disease of a Gramineous plant of the present invention can be performed in a manner such that a seed of a Gramineous plant is dressed, smeared, or sprayed with the agent. Alternatively, the method can be carried out by: soaking the seed of a Gramineous plant in a suspension of those microorganisms; or introducing a suspension containing those microorganisms or cells into a soil and then mixing the whole, or sparging the suspension or cells to a Gramineous plant itself in a farm field to spray foliages.

Further, the agent for controlling a disease of a Gramineous plant of the present invention does not interfere with other agents for controlling a disease of a plant when used in combination. For example, an insecticide, a nematicide, a miticide, a herbicide, a plant growth stimulator, a synergist, or the like can be used simultaneously together with the agent of the present invention after mixing or without mixing.

The agent for controlling a disease of a Gramineous plant of the present invention is effective for a disease occurring in a Gramineous plant. Examples of the disease to be effectively treated include diseases caused by, but not limited to, *Burkholderia plantarii*, *Burkholderia glumae*, *Acidodovorax avenae*, *Erwinia herboicola*, *Pseudomonas fuscovaginae*, *Xanthomonas campestris* pv. *oryzae*, *Pyricularia oryzae*, *Gibberella fujikuroi*, and *Cochliobolus miyabeanus*.

Furthermore, a biological material of the present invention is exemplified by a soil for raising seedling of a Gramineous plant, a medium for raising seedlings (such as rock wool), or a nursery box for raising seedling of a Gramineous plant which are treated with the controlling agent of the present invention.

Hereinafter, the present invention will be specifically described with reference to formulation examples and test examples, however the present invention is not limited to these examples.

TEST EXAMPLE 1

Efficacy to "Bakanae" Disease Caused by *Gibberella Fujikuroi*

Using infected rice seeds (cultivar: Tangin-bozu) which have been naturally infected by *Gibberella fujikuroi*, efficacy of *Penicillium* sp. B-453 (FERMBP-08517), *Eupenicillium* sp. B-408 (FERM BP-08515), and *Talaromyces* sp. B-422 (FERM BP-08516) on the disease by means of seed treatment were investigated. Each strain was cultured in a PDA medium at 25° C. for 10 days, and spores thereof were suspended in sterilized water to prepare a spore suspension having a predetermined concentration. The seeds infected by *Gibberella fujikuroi* were soaked in the spore suspension of the antagonistic fungi in a bath ratio of 1:1 for 24 hours and then the seeds were dipped (ratio of seeds to suspension is 1:1) at 30° C. for 3 days. After that, 5 g of dry seeds equivalent per pot were sown (each section has 3 replications) in a nursery box (10×15 cm) for raising seedling loaded with a commercial granulated soil for raising seedling (brand name: Kumiai granulated soil). Then, the seeds were germinated at 30° C. for 3 days and were grown in a glass green house thereafter. After 21 days from the sowing, ratios of incidence of seedlings in each test section were investigated to calculate preventive values

TABLE 1

| Strain | Spore concentration (cells/ml) | Number of investigated seedlings | Ratio of damping-off seedlings % | Ratio of elongated seedlings % | Ratio of diseased seedlings % | Preventive value |
|---|---|---|---|---|---|---|
| B-422 | $1.0 \times 10^6$ | 567 | 0.0 | 0.5 | 0.5 | 99.4 |
| B-453 | $1.0 \times 10^6$ | 568 | 0.0 | 0.7 | 0.7 | 99.2 |
| B-408 | $1.0 \times 10^6$ | 538 | 0.0 | 5.0 | 5.0 | 94.4 |
| No treatment | | 509 | 0.8 | 89.1 | 89.9 | 0.0 |

Tested Seed: Tangin-bozu (harvested in 2001, naturally infected seeds)
Seed treatment: 24 hours-dipping
Seed soaking: 15° C. for 4 days
Stimulation of germination: 30° C. for 1 day
Germination: 30° C. for 3 days

TEXT EXAMPLE 2

Efficacy to Rice Seedling Bright Caused by *Burkholderia Plantarii*

Using infected seeds (cultivar: Nihonbare) to which *Burkholderia plantarii* has been inoculated during the flowering period, Efficacy of *Talaromyces* sp. B-422 (FERM BP-08516) on the disease by means of seed treatment were investigated. The method of culturing the strain and the method of treating the seed are same as those in Test Example 1.

10 g of dry seeds equivalent per pot were sown (each section has 3 replications) in a nursery box (10×15 cm) for raising seedling loaded with a commercial granulated soil for raising seedling (brand name: Kumiai granulated soil). After 14 days from the sowing, each test section was investigated for the onset and progression of the disease using the following disease index. The results are shown in Table 2.

[Disease Index]

0: no incidence, 1: no damped-off seedling while some whitened seedlings exist, 2: damping-off seedlings are 25% or less, 3: damping-off seedlings are 25 to 50%, 4: damping-off seedlings are 50 to 80%, 5: damping-off seedlings are 80% or more (almost all the seedlings are blighted)

TABLE 2

| Strain | Spore concentration (cells/ml) | Average disease index | Average preventive value |
|---|---|---|---|
| B-422 | $1.0 \times 10^7$ | 1.2 | 73 |
| No treatment | | 4.3 | 0 |

Tested seed: H13 Nihonbare (seeds inoculated during the flowering period)
Seed treatment date: Apr. 2, 2003
Seed soaking: 15° C. for 4 days
Stimulation of germination: 30° C. for 1 day
Germination: 30° C. for 3 days
Investigation: 10 days after sowing

TEST EXAMPLE 3

Efficacy to Rice Seedling Rot Caused by *Burkholderia Glumae*

Using infected seeds (cultivar: Nihonbare) to which *Burkholderia glumae* has inoculated under reduced pressure, efficacy of *Talaromyces* sp. B-422 (FERM BP-08516) on the disease by means of seed treatment were investigated. The method of culturing the strain and the method of treating the seed are same as those in Test Example 1.

10 g of dry seeds equivalent per pot were sown (each section has 3 replications) in a nursery box (10×15 cm) for raising seedling loaded with a commercial granulated soil for raising seedling (brand name: Kumiai granulated soil). After 14 days from the sowing, each test section was investigated for the onset and progression of the disease using the following disease index. The results are shown in Table 3.

[Disease Index]

0: no incidence, 1: no damped-off seedling while some browning and partially damping-off seedlings exist, 2: damping-off seedlings are 25% or less, 3: damping-off seedlings are 25 to 50%, 4: damping-off seedlings are 50 to 80%, 5: damping-off seedlings are 80% or more (almost all the seedlings are damped-off)

TABLE 3

| Strain | Spore concentration (cells/ml) | Average disease index |
|---|---|---|
| B-422 | $5.6 \times 10^7$ | 0.0 |
| No treatment | | 1.0 |

Tested seed: Nihonbare (harvested in 2001, inoculated *Burkholderia glumae* under reduced pressure)
Seed treatment: 24 hours-dipping
Seed soaking: 15° C. for 4 days
Stimulation of germination: 30° C. for 1 day
Germination: 30° C. for 3 days (in a seedling raising apparatus)
Disease investigation: 10 days after the sowing

TEST EXAMPLE 4

Efficacy to Rice Seedling Sheath Blight Caused by *Acidodovorax Avenae*

Using infected seeds (cultivar: Nihonbare) to which *Acidodovorax avenae* has inoculated under reduced pressure, efficacy of *Eupenicillium* sp. B-408 (FERM BP-08515) on the disease by means of seed treatment were investigated. The method of culturing the strain and the method of treating the seed are same as those in Test Example 1.

10 g of dry seeds equivalent per pot were sown (each section has 3 replications) in a nursery box (10×15 cm) for raising seedling loaded with a commercial granulated soil for raising seedling (brand name: Kumiai granulated soil). Then, the seeds were germinated at 32° C. for 3 days and were grown in a glass green house thereafter. After 21 days from the seeding, ratios of infected seedlings in each test section were investigated to obtain preventive values. The results are shown in Table 4.

TABLE 4

| Strain | Spore concentration (cells/ml) | Number of investigated seedlings | Ratio of diseased seedlings (%) | Preventive value |
|---|---|---|---|---|
| B-408 | $1.0 \times 10^8$ | 1196 | 2.9 | 72.4 |
| No treatment | | 1054 | 10.6 | 0.0 |

Tested seed: Koshihikari (harvested in 1999, inoculated *A. avenae* MAFF3301505 under reduced pressure)
Seed soaking: 15° C. for 4 days
Stimulation of germination: 30° C. for 1 day
Seeding: dry seeds 10 g equivalent/pack
Germination: 32° C. for 3 days
Investigation: 17 days after sowing

TEST EXAMPLE 5

Efficacy to Rice Seedling Blast Caused by *Pyricularia Oryzae*

Using infected seeds (cultivar: Sasanishiki) which has been naturally infected by *Pyricularia oryzae*, efficacy of *Talaromyces* sp. B-422 (FERM BP-08516) on the disease by means of seed treatment were investigated. The method of culturing the strain and the method of treating the seed are same as those in Test Example 1.

10 g of dry seeds equivalent per pot were sown (no replication) in a nursery box (10×15 cm) for raising seedling loaded with a commercial granulated soil for raising seedling (brand name: Kumiai granulated soil). Then, the seeds were germinated at 32° C. for 4 days and were grown in a glass green house thereafter. After 21 days from the seeding, ratios of infected seedlings in each test section were investigated to obtain preventive values. The results are shown in Table 5.

TABLE 5

| Strain | Spore concentration (cells/ml) | Number of investigated seedlings | Ratio of diseased seedlings (%) | Preventive value |
|---|---|---|---|---|
| B-422 | $1.0 \times 10^7$ | 292 | 10.3 | 58.4 |
| " | $1.0 \times 10^6$ | 319 | 11.0 | 55.5 |
| " | $1.0 \times 10^6$ | 316 | 13.6 | 44.9 |
| No treatment | | 312 | 24.7 | 0.0 |

Tested seed: Sasanishiki (harvested in 2001)
Test scale: 10 g per section, one series
Seed treatment: 24 hours-dipping at 20° C.
Seed soaking: 20° C. for 3 days
Stimulation of germination: 30° C. for 1 day
Germination: 30° C. for 3 days
Investigation: 20 days after sowing

[Reference to Deposited Biological Materials]
(1)
a. Name and address of Depositary in which the present biological material has been deposited
International Patent Organism Depositary, National Institute of Advanced Industrial Science and Technology
Tsukuba Central 6, 1-1-1 Higashi, Tsukuba, Ibaraki, Japan (Postal code: 305-8566)
b. Date on which the biological material was deposited in the Depositary of the item (a)
Oct. 20, 2003 (original deposition date)
c. Accession number assigned upon the deposition by the Depositary of the item (a)
FERM BP-08517
(2)
a. Name and address of Depositary in which the present biological material has been deposited
International Patent Organism Depositary, National Institute of Advanced Industrial Science and Technology
Tsukuba Central 6, 1-1-1 Higashi, Tsukuba, Ibaraki, Japan (Postal code: 305-8566)
b. Date on which the biological material was deposited in the Depositary of the item (a)
Oct. 20, 2003 (original deposition date)
c. Accession number assigned upon the deposition by the Depositary of the item (a)
FERM BP-08515
(3)
a. Name and address of Depositary in which the present biological material has been deposited
International Patent Organism Depositary, National Institute of Advanced Industrial Science and Technology
Tsukuba Central 6, 1-1-1 Higashi, Tsukuba, Ibaraki, Japan (Postal code: 305-8566)
b. Date on which the biological material was deposited in the Depositary of the item (a)
Oct. 20, 2003 (original deposition date)
c. Accession number assigned upon the deposition by the Depositary of the item (a)
FERM BP-08516
International deposit number: FERM BP-08516
The complete taxonomic description of the deposited microorganism is as follows:
Talaromyces sp. B-422.
The deposit material has been accepted for deposit under the "Budapest Treaty on the International Recognition of the Deposit of Microorganisms" for purpose of patent procedure. All restrictions on the availability to the public of the material so deposited will be irrevocably removed upon the granting of a patent.

Date of deposit: Oct. 20, 2003

Name of depository: International Patent Organism Depository National Institute of Advanced Industrial Science and Technology Address of depository: AIST Tsukuba Central 6, 1-1, Higashi 1-Chome, Tsukuba-shi, Ibaraki-ken 305-8566, Japan

The invention claimed is:

1. A biologically pure culture of *Talaromyces* sp. B-422 strain having Accession No. FERM BP-08516.

2. A composition comprising a viable biologically pure culture of strain *Talaromyces* sp. B-422 strain having Accession No. FERM BP-08516 and a solid or liquid carrier, wherein the strain is present in an amount sufficient for controlling diseases caused by *Gibberella fujikuroi* and *Burkholderia plantarii*.

3. The composition according to claim 2 further comprising an insecticide, a nematicide, a miticide, a herbicide, or a plant growth stimulator.

4. A method for controlling diseases in gramineous plants caused by *Gibberella fujikuroi* and *Burkholderia plantarii*, wherein a gramineous plant, a gramineous plant seed, a soil for raising seedlings of a gramineous plant, a rock wool for raising seedlings of a gramineous plant, and/or a nursery box for raising seedlings of a gramineous plant is/are treated with an amount of a viable biologically pure culture of *Talaromyces* sp. B-422 strain having Accession No. FERM BP-08516 sufficient for controlling diseases caused by *Gibberella fujikuroi* and *Burkholderia plantarii*.

* * * * *